(12) United States Patent
Ballard et al.

(10) Patent No.: US 9,889,075 B2
(45) Date of Patent: Feb. 13, 2018

(54) DRY SHAMPOO COMPOSITION

(71) Applicant: Conopco, Inc., Englewood Cliffs, NJ (US)

(72) Inventors: Nicholas Ballard, Donostia-San Sebastian (ES); Stefan Antonius Franciscus Bon, Birmingham (GB); Ezat Khoshdel, Neston (GB); Glyn Roberts, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 110 days.

(21) Appl. No.: 15/029,664

(22) PCT Filed: Oct. 22, 2014

(86) PCT No.: PCT/EP2014/072607
§ 371 (c)(1),
(2) Date: Apr. 15, 2016

(87) PCT Pub. No.: WO2015/059169
PCT Pub. Date: Apr. 30, 2015

(65) Prior Publication Data
US 2016/0228340 A1    Aug. 11, 2016

(30) Foreign Application Priority Data
Oct. 22, 2013 (EP) .................... 13189640

(51) Int. Cl.
| | | |
|---|---|---|
| *C11D 3/12* | (2006.01) | |
| *C11D 3/18* | (2006.01) | |
| *C11D 3/37* | (2006.01) | |
| *C11D 3/38* | (2006.01) | |
| *A61K 8/19* | (2006.01) | |
| *A61Q 5/02* | (2006.01) | |
| *A61K 8/81* | (2006.01) | |
| *A61K 8/02* | (2006.01) | |
| *A61K 8/04* | (2006.01) | |
| *A61K 8/37* | (2006.01) | |

(52) U.S. Cl.
CPC .............. *A61K 8/19* (2013.01); *A61K 8/0245* (2013.01); *A61K 8/0279* (2013.01); *A61K 8/046* (2013.01); *A61K 8/37* (2013.01); *A61K 8/8117* (2013.01); *A61K 8/8152* (2013.01); *A61Q 5/02* (2013.01); *C11D 3/1206* (2013.01); *A61K 2800/31* (2013.01); *A61K 2800/41* (2013.01); *A61K 2800/412* (2013.01); *A61K 2800/413* (2013.01); *A61K 2800/47* (2013.01); *A61K 2800/624* (2013.01); *A61K 2800/651* (2013.01)

(58) Field of Classification Search
CPC ....... C11D 3/1206; C11D 3/18; C11D 3/3761; C11D 17/0043
USPC ................................ 510/120, 130, 441, 475
See application file for complete search history.

(56) References Cited

U.S. PATENT DOCUMENTS

| | | | |
|---|---|---|---|
| 4,328,319 | A | 5/1982 | Osipow |
| 2007/0245500 | A1 | 10/2007 | Brun |
| 2008/0254074 | A1 | 10/2008 | Dussaud |

FOREIGN PATENT DOCUMENTS

| | | |
|---|---|---|
| DE | 2752320 | 6/1978 |
| EP | 1627664 | 2/2006 |
| EP | 1914264 | 4/2008 |
| EP | 1967172 | 9/2008 |
| GB | 1581377 | 12/1980 |
| JP | 2004043558 | 2/2004 |
| KR | 20130114986 | 10/2013 |
| WO | WO9959530 | 11/1999 |
| WO | WO03028678 | 4/2003 |
| WO | WO03028682 | 4/2003 |
| WO | WO2007104089 | 9/2007 |
| WO | WO2011056625 | 5/2011 |
| WO | WO2012104362 | 8/2012 |
| WO | WO2012143700 | 10/2012 |
| WO | WO2013143792 | 10/2013 |
| WO | WO2013143935 | 10/2013 |

OTHER PUBLICATIONS

Sunjin Chemical, Sunjin Brochure, 10th Ed., Part 14: Skin Care, Apr. 2012 Apr. pp. 1-48. pp. 1 to 48.
AkzoNobel Product Brochure, Surface Chemistry Dry-Flo® TS Starch/Dry Flo® TS Pure Starch, Jan. 5, 2012 (Rev. Jan. 22, 2014) pp. 1-7, XP055108311. pp. 49 to 55.
Mintel GNPD, Drybar Products, USA, Detox Dry Shampoo, Mar. 2013, Record ID 2022808, XP055106227. pp. 56 to 60.
IPRP2 in PCTEP2014072607 dated Jan. 22, 2016. pp. 1 to 12.
Search Report & Written Opinion in EP13189640 dated Mar. 27, 2014. pp. 13 to 20.
Search Report & Written Opinion in PCTEP2014072607 dated Feb. 11, 2015. pp. 21 to 39.
Mintel GNPD, Alberto Culver Tresemme Fresh Start Dry Shampoo, Feb. 2012, Record ID 1727707, XP002683580. pp. 1 to 2.
Mintel GNPD, pH Beauty Labs Pssssst! Instant Dry Shampoo, Nov. 2011, Record ID 1669958, XP002683579. pp. 3 to 4.

*Primary Examiner* — Gregory R Delcotto
(74) *Attorney, Agent, or Firm* — Karen E. Klumas

(57) ABSTRACT

Cleaning composition, which is a dry shampoo, comprising a base and propellant, wherein the base comprises sebum absorber which comprises magnetic particles, wherein the magnetic particles have a particle size in the range of from 4 nm to 50 nm, and wherein the magnetic particles are coated with a stabilizing dispersing agent, and wherein the magnetic particles are dispersed in a liquid carrier.

11 Claims, No Drawings

DRY SHAMPOO COMPOSITION

The present invention relates to a dry shampoo composition comprising sebum absorbers, for application to hair.

Dry shampoos are compositions for cleansing the hair without washing with water. The product provides a suitable product to provide a clean feel and look on days when perhaps there is no opportunity, either through lack of time or lack of available water, to wash the hair.

Database GNPD [Online] Mintel November 2011 (2011-11) "Instant Dry Shampoo" XP002683579 Database accession no. 1669958 discloses a dry shampoo comprising aluminium starch octenylsuccinate, silica and glycerine. The composition also comprises butylenes glycol.

Database GNPD [Online] Mintel February 2011 (2012-02) "Instant Dry Shampoo" XP002683580 Database accession no. 1727707 discloses a dry shampoo comprising aluminium starch octenylsuccinate, silica and glycerine. The composition also comprises butylenes glycol.

Current dry shampoo technology typically employ hydrophobically modified starches. However, these particles are poor sebum absorbers. Furthermore the sebum imbibed starch particles are soft and difficult to remove from hair fibres resulting in sticky and unclean hair. In addition, starch particles can cause the appearance of white particles on hair, which is undesirable for the user. To combat this problem formulators must add coloured pigments to mask the white particles. Thus there is a need to develop robust particles that have high sebum absorption properties, fast kinetics to remove maximum sebum from hair fibres rapidly that can be removed readily.

We have surprisingly found that an improved dry shampoo can be formulated with magnetic particles having a particle size in the range of from 4 nm to 50 nm and are dispersed in a liquid carrier. The particles are applied to the hair in the usual manner and removed by applying a magnetic comb or brush over or through the hair. The particles are attracted to the magnet and removed from the hair. No white residue is left. The consumer is thus provided with a simple yet effective means for cleaning the hair on a non-wash day.

Accordingly, and in a first aspect, the present invention provides a cleaning composition, which is a dry shampoo, comprising a base and propellant, wherein the base comprises sebum absorber which comprises magnetic particles, wherein the magnetic particles have a particle size in the range of from 4 nm to 50 nm, and wherein the magnetic particles are coated with a stabilizing dispersing agent, and wherein the magnetic particles are dispersed in a liquid carrier.

Preferably, the composition comprises substantially no alcohol. More preferably the composition comprises substantially no ethanol. More preferably, the composition comprises from 0 to 2% wt., most preferably 0 to 1% wt. of the composition alcohol. More preferably, the composition comprises from 0 to 2% wt., more preferably from 0 to 1% wt. of the composition ethanol.

Preferably, the base comprises from 5 to 20% wt. of the composition.

Preferably, the base comprises from 2 to 75% wt of the base sebum absorber.

The magnetic particles for use in the invention consist of sub-domain magnetic particles having an average particle size of from 4 to 50 nm, preferably from 5 to 20 nm, most preferably 10 nm.

Preferred particles are ferromagnetic magnetite.

The magnetic particles are in the form of a suspension, in a liquid carrier, preferably an oil. The oil is preferably selected from a mineral oil, a vegetable oil and a silicone oil.

Preferred vegetable oils are selected from sunflower oil, rapeseed oil, olive oil, macadamia oil, pomegranate oil, coconut oil and sweet almond oil.

Preferred mineral oils are selected from paraffinic oils, hydrocarbon oils, aromatic oils, and naphthenic oils and fatty esters. Preferred examples are hexane, hexanol, cyclohexanol, toluene and naphthalene.

Preferred silicone oils are selected from low molecular weight cyclodimethicones, linear, branched, hyperbranched and star polysiloxanes, for example dimethiconols, polydimethylsiloxanes and amino silicones. Commercial examples include: Dow Corning® Q7-9120 silicone fluid, 12,500, Wacker® AK 50 silicone fluid and Wacker® AK 100 Silicone. Preferred amino silicones are amodimethicones, for example DC8500, INCI Name Bis (C13-C15) PG Amodimethicone.

Alkylmethylsiloxanes (AMS) INCI Name: C 30-45 Alkylmethicone (Dow Corning® ST-Wax 30)

The magnetic particles are coated with a stabilizing dispersing agent, preferably an oil soluble surfactant or an oil emulsifier. Preferred oil soluble surfactants or oil emulsifiers have HLB values of from 3 to 10. Examples of oil soluble commercial surfactants include: TERGITOL NP-4 to NP-7, Triton X-15, X-35 and X-45, and TERGITOL 15-S-3 and 15-S-5, available from Dow Chemicals.

The particle suspension (i.e. magnetic particles in oil) preferably contains by volume 2 to 20%, preferably 5 to 10% magnetic solid, from 1 to 20%, preferably 5 to 15%, most preferably 10% stabilising dispersing agent, and 70 97%, preferably 75 to 90%, most preferably 85% liquid carrier.

Preferably, the magnetic particles comprise styrene/polydivinylbenzene copolymer.

Preferably, the magnetic particles comprise hydrophobic acrylate, which preferably comprises a hydrophobic group. Preferably, the hydrophobic group comprises an alkyl group. Preferably, the alkyl group comprises from 8 to 22 carbons. Preferred acrylates include lauryl methacrylate, 2-ethyl hexyl methacrylate and butyl acrylate.

Most preferred magnetic particles are Ferrofluids available, for example, from Ferrotec Gmbh, or E-Magnets UK.

Preferably, the sebum absorbers have an average particle size d(0.5) as measured using a Malvern (DLS) Mastersizer 2000 from 20 to 120 microns, more preferably from 30 to 90 microns.

Preferably, the dry shampoo comprises an oil which is preferably present at from 0.1 to 5% wt. of the base.

Preferably, the oil is isopropyl myristate, benzyl alcohol, PPG-3 benzyl ether myristate. The most preferred is isopropyl myristate.

Preferably, the dry shampoo comprises propylene glycol. Preferably any propylene glycol is present at from 0.5 to 5% wt. of the base.

In a composition according to the invention the propylene glycol reduces or prevents white residues being deposited on the hair. This is particularly problematic for users with dark hair.

The composition of the invention also comprises a propellant to suspend the base immediately before mixing and to facilitate its egress from its container.

The composition is stored in a pressurised container. Preferably, the container is an aerosol canister. More preferably, the container is an un-lacquered aerosol canister.

Suitable propellants are well known in the art and include butane, isobutene and propane.

EXAMPLE

A virgin hair switch was treated with the control by way of applying sebum directly to the switch.

The switch was then treated with a dry shampoo composition comprising one of the test particles and the particles then removed with a magnet. The amount of sebum remaining was then measured as a percentage of that which was applied.

TABLE 1

| Sample | DVB | Acrylate | Ratio (DVB/Acrylate) | Sebum Removal (% remaining) |
|---|---|---|---|---|
| Control | — | — | — | 86.67 |
| PDVB 1 | Divinyl Benzene | — | — | 14.71 |
| PDVB 2 | Divinyl Benzene | Lauryl methacrylate | 1:0.1 | 46.15 |
| PDVB 3 | Divinyl Benzene | 2-Ethylhexyl methacrylate | 1:0.1 | 15.38 |
| PDVB 4 | Divinyl Benzene | Butyl acrylate | 1:0.1 | 21.05 |
| PDVB 5 | Divinyl Benzene | Lauryl methacrylate | 1:0.3 | 0 |

Particles were magnetized using Ferrofluid via suspension polymerisation. The ferrofluid encapsulated inside micro particles.

Synthesis of Magnetic Porous Particles

Magnetic porous particles were prepared by suspension polymerization in a 1 L reactor equipped with a mechanical stirrer and nitrogen inlet according to the recipes shown in Table 2. The heterogeneous reaction mixture was degassed for half an hour whilst being stirred at 500 rpm. The nitrogen source was then raised above the solution and the stirring rate was dropped to 350 rpm. The reaction was allowed to proceed for 18 h at 70° C. The resulting porous particles were collected by filtration and washed by distilled water and ethanol. The particles were then left in 1 L of acetone solution stirring overnight to completely remove any linear polymer. The final product was filtered again and dried in vacuo for 24 hours at 60° C.

TABLE 2

| | Sample 1 | 2 | 3 | 4 | 5 |
|---|---|---|---|---|---|
| Divinylbenzene (DVB) | 40 g | 40 g | 40 g | 40 g | 40 g |
| Lauryl methacrylate | | 4 g | | | |
| 2-Ethylhexyl methacrylate | | | 4 g | | |
| Butyl acrylate | | | | 4 g | |
| Ferrofluid (20 wt % in toluene) | 5 g | 5 g | 5 g | 5 g | 10 g |
| AIBN | 0.6 g | 0.6 g | 0.6 g | 0.6 g | 0.6 g |
| Toluene | 100 ml | 150 ml | 150 ml | 150 ml | 200 ml |
| Polyvinyl alcohol | 12 g | 12 g | 12 g | 12 g | 12 g |
| NaCl | 12 g | 12 g | 12 g | 12 g | 12 g |

The suitable amount of ferrofluid for better magnetic action was achieved by using magnetic particles in ratio of 1:0.25 (DVB:Ferrofluid). Lowering the ratio of ferrofluid did not cause any significant magnetic action.

TABLE 3

The following are formulations for dry shampoos comprising magnetic particles. They are made by standard processes and comprise any of the magnetic particles described in Table 1.

| INCI names | Dry Shampoo |
|---|---|
| SD Alcohol 40-B (Alcohol Denat.) | 13.510 |
| Isopropyl Myristate | 0.250 |
| Magnetic Particles | 1.875 |
| Silica | 0.065 |
| Fragrance (Parfum) | 0.300 |
| Isobutane (85%), Propane (15%) | 84 |
| | 100.000 |

The invention claimed is:

1. Cleaning composition, which is a dry shampoo, comprising a base and propellant, wherein the base comprises a sebum absorber which comprises magnetic particles, wherein the magnetic particles have a particle size in the range of from 4 nm to 50 nm, and wherein the magnetic particles are coated with a stabilizing dispersing agent, and wherein the magnetic particles are dispersed in a liquid carrier.

2. Composition according to claim 1, wherein the liquid carrier is an oil.

3. Composition according to claim 1 wherein the base comprises from 5 to 20% wt. of the composition.

4. Composition according to claim 1 wherein the base comprises from 2 to 75% wt of the base, the sebum absorber.

5. Composition according to claim 1 wherein the sebum absorber comprises particles of average particle size from 20 to 120 micrometer.

6. Composition according to claim 1 wherein the particles comprise styrene/polydivinylbenzene copolymer.

7. Composition according to claim 1 wherein the particles comprise acrylate.

8. Composition according to claim 7 wherein the acrylate is a hydrophobically modified acrylate.

9. Composition according to claim 8, wherein the hydrophobically modified acrylate comprises an alkyl group comprising from 8 to 22 carbons.

10. Composition according to claim 1 comprising an oil from 0.1 to 5% wt. of the base.

11. Composition according to claim 10 wherein the oil is isopropyl myristate.

* * * * *